United States Patent
Nett et al.

(10) Patent No.: US 9,836,862 B2
(45) Date of Patent: Dec. 5, 2017

(54) METHODS AND SYSTEMS FOR CONTRAST ENHANCED IMAGING WITH SINGLE ENERGY ACQUISITION

(71) Applicant: General Electric Company, Schenectady, NY (US)

(72) Inventors: Brian Edward Nett, Brookfield, WI (US); Hewei Gao, Pewaukee, WI (US); Paavana Sainath, North Haledon, NJ (US)

(73) Assignee: General Electric Company, Schenectady, NY (US)

( * ) Notice: Subject to any disclaimer, the term of this patent is extended or adjusted under 35 U.S.C. 154(b) by 422 days.

(21) Appl. No.: 14/586,663

(22) Filed: Dec. 30, 2014

(65) Prior Publication Data
US 2016/0189402 A1   Jun. 30, 2016

(51) Int. Cl.
*G06K 9/00* (2006.01)
*A61B 6/00* (2006.01)
*G06T 11/00* (2006.01)

(52) U.S. Cl.
CPC ............ *G06T 11/008* (2013.01); *A61B 6/481* (2013.01); *A61B 6/482* (2013.01); *A61B 6/5205* (2013.01); *A61B 6/5211* (2013.01); *A61B 6/5217* (2013.01); *A61B 6/5258* (2013.01); *A61B 6/585* (2013.01); *G06T 2211/421* (2013.01); *G06T 2211/424* (2013.01)

(58) Field of Classification Search
USPC ........ 382/100, 103, 106–107, 128–134, 162, 382/173, 181, 199, 232, 254, 274, 276, 382/286, 291, 312; 378/5, 4, 21; 345/617
See application file for complete search history.

(56) References Cited

U.S. PATENT DOCUMENTS

| | | | |
|---|---|---|---|
| 5,687,208 A | 11/1997 | Bae et al. | |
| 7,280,635 B2 | 10/2007 | Toth | |
| 7,583,779 B2 | 9/2009 | Tkaczyk et al. | |
| 8,363,917 B2 * | 1/2013 | Fan ..................... | G06T 11/008 378/4 |
| 8,811,709 B2 | 8/2014 | Wu et al. | |
| 2006/0025680 A1 | 2/2006 | Jeune-Iomme et al. | |
| 2009/0052612 A1 * | 2/2009 | Wu ....................... | A61B 6/032 378/5 |

(Continued)

OTHER PUBLICATIONS

Siemens, "Get further. With True Dual Energy.", Available as early as Jan. 1, 2014, 12 pages.

(Continued)

*Primary Examiner* — Seyed Azarian
(74) *Attorney, Agent, or Firm* — McCoy Russell LLP (57) ABSTRACT

Methods and systems are provided for boosting the contrast levels in an image reconstructed from projection data acquired at a single energy. In one embodiment, a method comprises modifying projection data corresponding to a material based on an absorption behavior of the material at a selected energy, wherein the projection data is acquired at an energy higher than the selected energy. In this way, contrast levels may be enhanced in an image reconstructed from projection data acquired at a typical single energy as though the image were reconstructed from projection data acquired at a lower energy.

22 Claims, 5 Drawing Sheets

(56) References Cited

U.S. PATENT DOCUMENTS

| | | | |
|---|---|---|---|
| 2012/0076258 A1* | 3/2012 | Chandra | A61B 6/03 378/5 |
| 2013/0116554 A1 | 5/2013 | Kaiser et al. | |
| 2014/0133719 A1* | 5/2014 | Wu | G06T 7/0012 382/131 |
| 2016/0189402 A1* | 6/2016 | Nett | G06T 11/008 345/617 |

OTHER PUBLICATIONS

Sakane, Makoto, et al. "Effects of High-concentration contrast material and low-voltage CT on contrast for multiphasic CT of the upper abdomen: comparison using the simulation with virtual monochromatic imaging obtained by fast-switch kVp dual-energy CT", Springerplus, vol. 3, No. 234, May 8, 2014, 9 pages.

Gao, Hewei, et al., "Revolution CT: Overcoming wide coverage IQ challenges", GE Healthcare, Available as early as Mar. 2014, 7 pages.

Itatani, R., et al. "Reduction in radiation and contrast medium dose via optimization of low-kilovoltage CT protocols using a hybrid iterative reconstruction algorithm at 256-slice body CT: phantom study and clinical correlation." Clinical Radiology vol. 68, No. 3, Mar. 2013, 8 pages.

* cited by examiner

METHODS AND SYSTEMS FOR CONTRAST ENHANCED IMAGING WITH SINGLE ENERGY ACQUISITION

FIELD

Embodiments of the subject matter disclosed herein relate to non-invasive diagnostic imaging, and more particularly, to boosting contrast levels in reconstructed images.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

A contrast agent such as iodine may be utilized to distinguish, for example, anatomical structures in a human body from surrounding soft tissue. However, the attenuation of x-rays by such contrast agents depends on the energy of the x-rays. For conventional CT imaging systems that acquire projection data at a single energy, it may be difficult to distinguish contrast-filled regions of the human body. As a result, typical approaches to enhancing contrast in such systems include an increase of contrast dosage and/or radiation dosage. Dual energy systems overcome this obstacle by acquiring projection data at a higher energy and a lower energy, where the higher energy typically corresponds to the aforementioned single energy of non-spectral CT imaging systems and the attenuation by the contrast agent is greater for photons at the lower energy. However, it remains desirable to enhance the contrast levels for non-spectral CT imaging systems without an increase of contrast dosage or radiation dosage.

BRIEF DESCRIPTION

In one embodiment, a method comprises modifying projection data corresponding to a material based on an absorption behavior of the material at a selected energy, wherein the projection data is acquired at an energy higher than the selected energy. In this way, contrast levels may be enhanced in an image reconstructed from projection data acquired at a typical single energy as though the image were reconstructed from projection data acquired at a lower energy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of medical imaging systems. In particular, methods and systems are provided for boosting the contrast levels in an image reconstructed from projection data acquired at a single energy. An example of a computed tomography (CT) imaging system that may be used to acquire images processed in accordance with the present techniques is provided in FIGS. 1 and 2. Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

Figure 4:
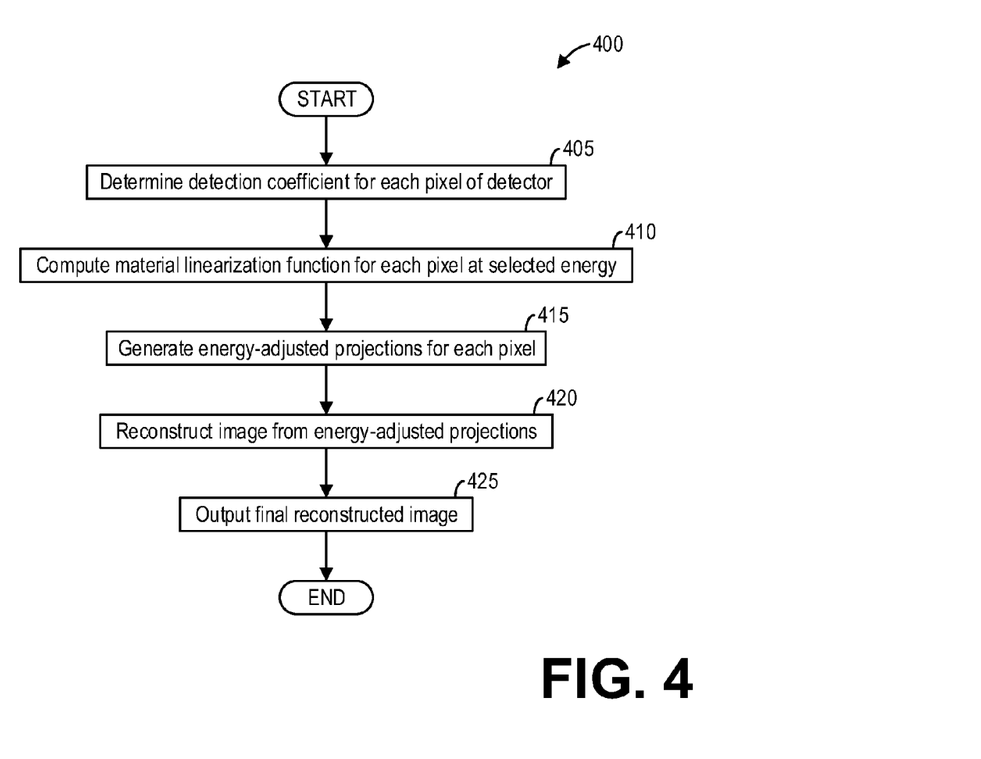
FIG. 4 is a high-level flow chart illustrating an example method for reconstructing an image from projection data modified to model a low energy acquisition according to an embodiment of the invention.
Figure 5:
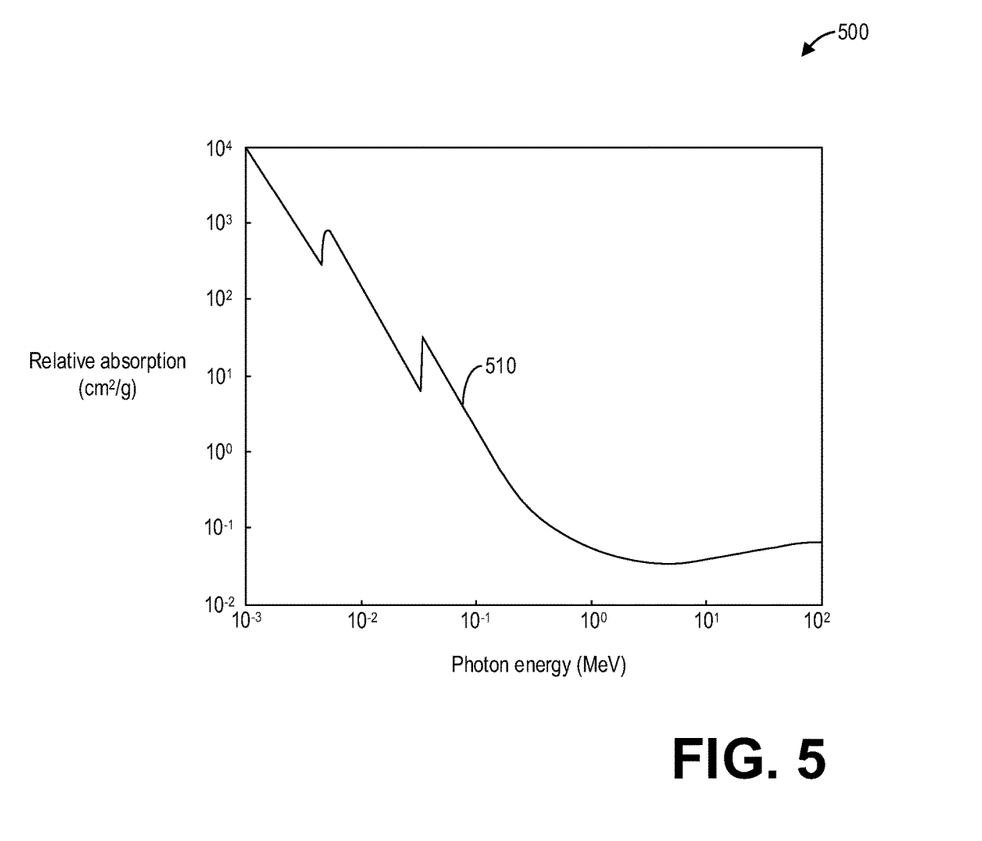
FIG. 5 is a graph illustrating an example absorption by a material as a function of photon energy according to an embodiment of the invention.
Figure 6:
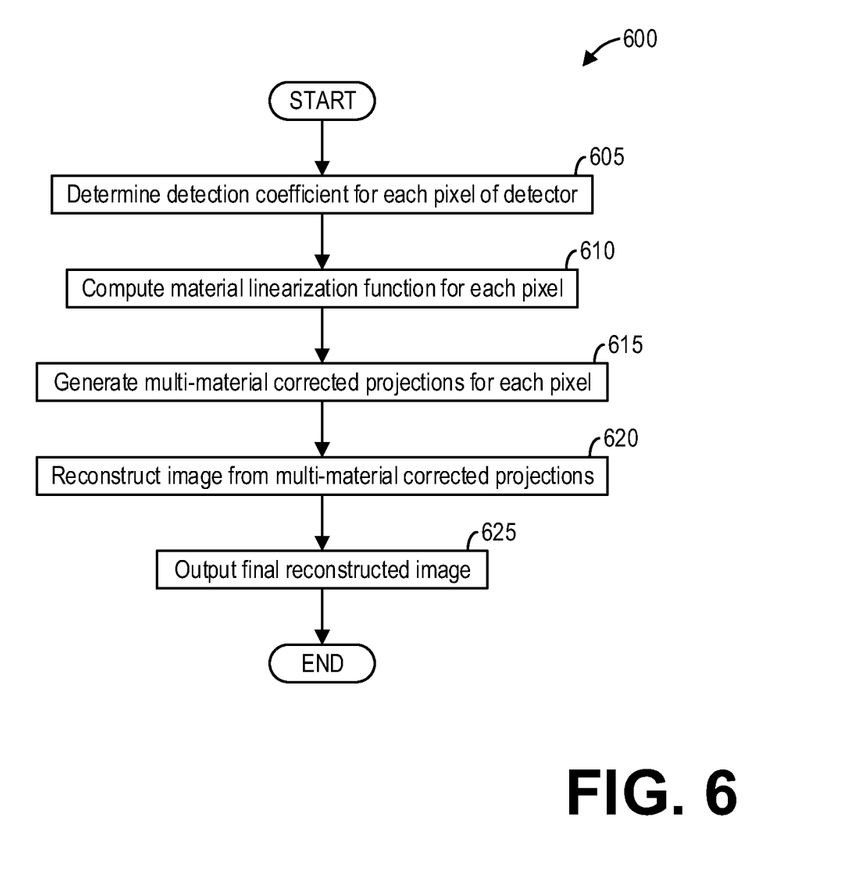
FIG. 6 is a high-level flow chart illustrating an example method for reconstructing an image from projection data modified by a multi-material correction according to an embodiment of the invention.

In CT imaging, there is an inherent tradeoff between the relative contrast-to-noise ratio and the x-ray dose and contrast dose delivered. A method for generating a contrast-enhanced image reconstructed from projection data acquired at a single energy, such as the method depicted in FIG. 3, enables a reduction in x-ray dose and contrast dose while providing the benefits of say, a dual energy imaging system which may require a larger x-ray and contrast dose. The method may comprise blending two images reconstructed from modified projection datasets. For example, as depicted in FIG. 4, one of the images may be reconstructed from projection data modified to simulate a lower energy data acquisition. As a result, the contrast in the reconstructed image may be boosted in accordance with the attenuation of a contrast agent at the simulated lower energy, as depicted in FIG. 5. However, an image reconstructed in such a manner may include beam-hardening artifacts. Therefore, the second image may be reconstructed from a multi-material corrected projection dataset, as depicted in FIG. 6, which may be substantially free of beam-hardening artifacts. In this way, the final image resulting from the blending of the two images may comprise a contrast-enhanced image free of beam-hardening artifacts.

Figure 1:
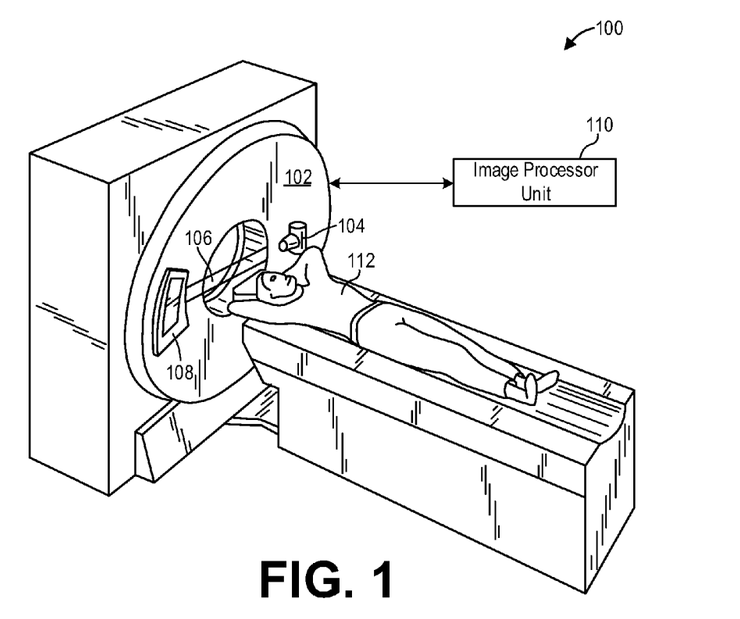
FIG. 1 is a pictorial view of an imaging system according to an embodiment of the invention.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered back projection (FBP) to reconstruct images of a target volume of the patient. As another example, the image processing unit 110 may use an iterative image reconstruction approach such as conjugate gradient (CG), maximum likelihood expectation maximization (MLEM), or model-based iterative reconstruction (MBIR) to reconstruct images of a target volume of the patient.

Figure 2:
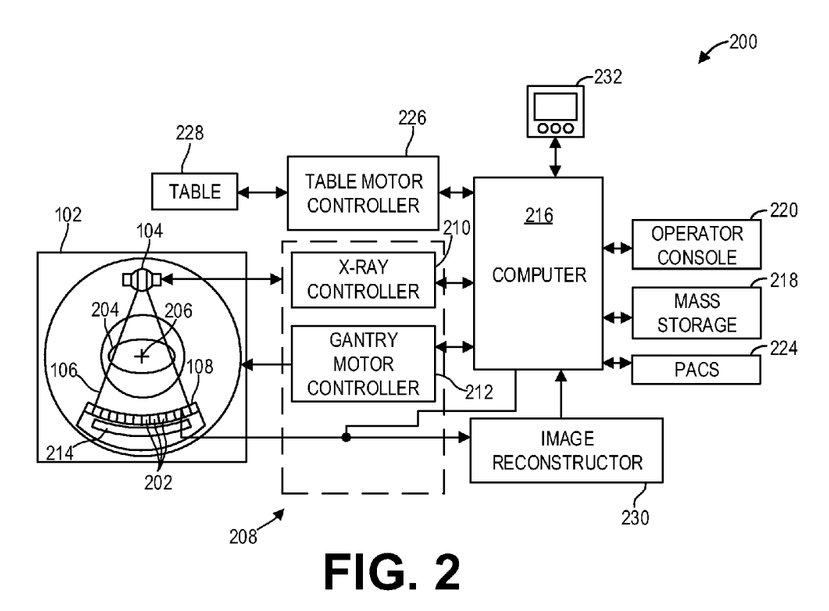
FIG. 2 is a block schematic diagram of an exemplary imaging system according to an embodiment of the invention.

FIG. 2 illustrates an exemplary imaging system 200 similar to the CT system 100 of FIG. 1. In accordance with aspects of the present disclosure, the system 200 is configured to reconstruct images with a user-specified temporal window in real-time. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in system 200. In one embodiment, image reconstructor 230 may include such instructions in non-transitory memory, and may apply the methods after reconstructing an image from scanning data. In another embodiment, computing device 216 may include the instructions in non-transitory memory, and may apply the methods to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

Figure 3:
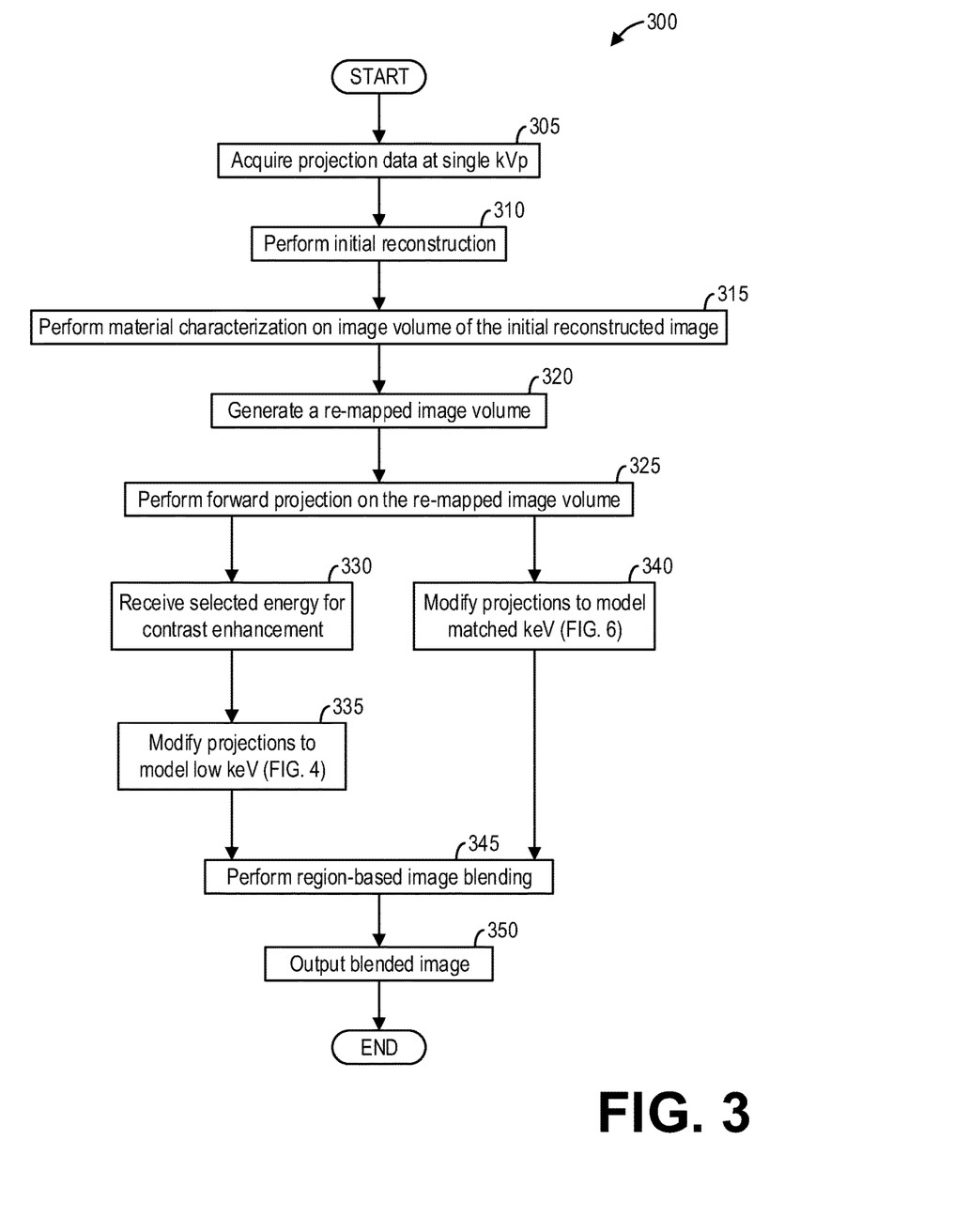
FIG. 3 is a high-level flow chart illustrating an example method for boosting contrast levels in certain portions of a reconstructed image according to an embodiment of the invention.

FIG. 3 is a high-level flow chart illustrating an example method 300 for boosting contrast levels in certain portions of a reconstructed image according to an embodiment of the invention. In particular, method 300 relates to the blending of two images to create a final reconstructed image, where the two images are each reconstructed from modified projection datasets respectively corresponding to a modeled low energy acquisition and a multi-material correction. Method 300 may be carried out using the systems and components depicted in FIGS. 1 and 2, however the method may be applied to other systems and components without departing from the scope of the present disclosure.

Method 300 may begin at 305. At 305, method 300 may include acquiring projection data at a single energy level, or tube peak kilovoltage (kVp). In some examples, a typical tube kVp for data acquisition may be on the order of 100-140 kVp. At 310, method 300 may include performing an initial reconstruction of the acquired projection data to generate an initial reconstructed image.

At 315, method 300 may include performing material characterization on an image volume of the initial reconstructed image. Performing material characterization may comprise sequentially performing material segmentation and inverse basis material decomposition. For example, the reconstructed image may be segmented based on Hounsfield units (HU) values of image volumes, or voxels, where the different materials in the image are separated based on designated HU levels and/or ranges representative of each material. Upon performing material segmentation, inverse basis material decomposition may be performed on the different segmented projection data. In particular, the inverse basis material decomposition transforms or converts the materials other than iodine and water (i.e., bone and metal) to the basis materials iodine and water.

At 320, method 300 may include generating a re-mapped image volume, for example, a material-based projection from a re-mapped pixel, for at least one basis material (e.g., iodine) of the two basis materials (e.g., iodine and water). In some examples, re-mapped projections may be obtained for both basis materials (e.g., iodine and water).

At 325, method 300 may include performing a forward projection on the re-mapped image volume to generate a forward projection for at least one basis material (e.g., iodine) to produce a material-based (e.g., iodine-based) projection. The image volume is forward-projected using the exact system geometry, and the forward projections are interpolated into the same ray directions and the same number of views as the measured projections by the detection system, which results in paired data projection sets.

At 330, method 300 may include receiving a selected energy for contrast enhancement. At 335, method 300 may include modifying the projection data to model a low energy (i.e., a low keV or kVp) acquisition. Modifying the projection data to model a low energy acquisition may comprise generating a mapping function based on the detection coefficients and the attenuation coefficient of a material (i.e., iodine) at the selected energy. Modifying the projection data may further comprise generating energy-adjusted projections for each pixel based on the mapping function and reconstructing an image from the energy-adjusted projections. Modifying the projection data to model a low energy acquisition is described further herein with regard to FIG. 4.

At 340, method 300 may include modifying the projection data to model matched keV. Modifying the projection data to model a matched energy (e.g., for multi-material correction) may comprise computing a material linearization function for each pixel at the effective energy (i.e., the acquisition energy), generating multi-material corrected projections for each pixel based on the material linearization function, and reconstructing an image from the multi-material corrected projections. Modifying the projection data to model a matched energy (e.g., for multi-material correction) is described further herein and with regard to FIG. 6.

The contrast may be enhanced in the image reconstructed from the energy-adjusted projections. However, additional beam-hardening artifacts may be introduced in the image. Since beam-hardening artifacts are removed from the multi-material corrected projections as well as the image reconstructed from said projections, at 345, method 300 may include performing region-based image blending of the two images. Blending the images may comprise selecting a Hounsfield unit (HU) for an image volume based on the low energy image, the matched energy image, and a soft threshold. The blending may be carried out in the frequency domain, and so in some examples blending the images may comprise Fourier transforming the image data into frequency space, combining the images, and inverse Fourier transforming the combined frequency data back into image space to produce a single Fourier blended image. In some examples, the blending may be limited to the regions characterized as containing at least one basis material (e.g., iodine). That is, in the regions of contrast enhancement, the values from the high contrast image (i.e., the low energy image) may be used, whereas in the soft tissue areas (i.e., the regions not containing iodine) the values from the least artifact image (i.e., the matched energy image) may be used. The soft threshold may be used when selecting an HU value at the boundary of the segments such that additional artifacts possibly introduced by a hard threshold may be avoided. The resulting blended image may include the contrast-enhanced regions with a substantial reduction of beam hardening artifacts.

At 350, method 300 may include outputting the blended image. The blended image may be output to a display 232 for display, for example, to a physician or operator and/or saved in mass storage 218 for reviewing at a later time. Method 300 may then end.

FIG. 4 is a high-level flow chart illustrating an example method 400 for reconstructing an image from projection data modified to model a low energy acquisition according to an embodiment of the invention. Method 400 may comprise a subroutine of method 300. In particular, method 400 may comprise the step 335. Thus, the projection data acquired at 305, the forward projection of the re-mapped image volume at 325, the selected energy received at 330, and so on may be available for use during the execution of method 400. Method 400 may be carried out using the systems and components depicted in FIGS. 1 and 2, however the method may be applied to other systems and components without departing from the scope of the present disclosure.

Method 400 may begin at 405. At 405, method 400 may include determining detection coefficients for each pixel of the detector array 108. The detection coefficients are obtained once for each pixel and may be used for subsequent scans. The detection coefficients are a function of the incident photon energy of each individual pixel. The detection coefficients may be captured, for example, from the data of four kVp air scans during spectral calibration. The detection coefficients enable the modeling of the detector signals. The detection coefficient of pixel i may be expressed in polynomial form as:

$$\epsilon(E,i) = \Sigma_0^{N-1} X_n(i) E^n,$$

where $\epsilon(E, i)$ is the detection coefficient, E is the photon energy, i is the pixel index, $X_n(i)$ are detection coefficients expressed in polynomial form, and N is the number of kVp air scans during the spectral calibration. In one example, N is based on the number of kVp stations. For example, N may range from 4 to 5. The detection efficiency factor may depend on a number of factors such as different kVps and different filtrations. In some examples, the $X_n(i)$ values may be stored, for example, in memory for use as described further herein.

At 410, method 400 may include computing a material linearization function for each pixel at a selected energy. The detection coefficients may be utilized in computing a material linearization function (for example, a mapping function) for each pixel using projections synthesized through system modeling. The mapping function for each pixel is designed to linearize material projections for the respective pixel. In general, the detected signals may be re-mapped so that the signals are all linearly proportional to each of the material's length with proper slope. The slope is a fixed value for each individual material that does not change from view to view. In one example, the slope may be set to the attenuation coefficient at the selected energy (i.e., keV) of the photon beam. The selected energy may comprise, for example, the selected energy received at step 330 in FIG. 3. In this way, the acquisition of projection data at the selected energy may be modeled, thereby simulating the increased (or in some examples, decreased) attenuation by a material, such as iodine, at the selected energy compared to the attenuation by the material at the actual acquisition energy.

For example, FIG. 5 is a graph 500 illustrating an example absorption by a material as a function of photon energy. In particular, plot 510 shows the relative absorption of iodine as a function of energy. As the photon energy decreases, the relative absorption (i.e., the attenuation coefficient) of iodine substantially increases. By computing the mapping functions for each pixel based on the known attenuation at a selected energy given by plot 510, the present simulation of data acquisition at a lower energy may be based on an empirical model. The resulting corrections may therefore produce an image including contrast levels expected in an image reconstructed from projection data acquired at the selected energy.

Returning to FIG. 4, the mapping functions may be obtained by computing a total raw projection of each pixel attenuated through a thickness of water $L_w$ and a thickness of iodine $L_{io}$ as given by:

$$P_t = -\log\left(\frac{\sum_E^{kv} S_{kv}(E) \cdot E \cdot e^{-\mu_w(E)L_w - \mu_{io}(E)L_{io}} \cdot \eta(E) \cdot \epsilon(E)}{\sum_E^{kv} S_{kv}(E) \cdot E \cdot \eta(E) \cdot \epsilon(E)}\right),$$

where index kv is the tube voltage at a given detector row location, E is the photon energy, $S_{kv}(E)$ is the incident spectrum, $\eta(E)$ is the scintillator stopping power, $\mu_w(E)$ is the water mass attenuation coefficient, $\mu_{io}(E)$ is the iodine mass attenuation coefficient, and $\epsilon(E)$ is the detection coefficient.

At 415, method 400 may include generating energy-adjusted projections for each pixel. The energy-adjusted projections may be based on a summation of the initial total projection and the material linearization function. In particular, the energy-adjusted projections may comprise the sum of the initial total projection $P_t$ and the energy corrections:

$$P_{corr} = P_t + \Delta p,$$

where the energy corrections $\Delta p$ may comprise the difference between the sum of the monochromatic signals and the polychromatic signal, as represented by:

$$\Delta p(P_r, P_{io}) = (\mu_1 L_w + \mu_2 L_{io}) - P_t,$$

where $\mu_1$ and $\mu_2$ are the attenuation coefficients of water and iodine respectively at the selected energy. The correction may be performed in the projection domain or the image domain if the initial image volume and the final volume are both reconstructed with full field of view. However, in clinical cases, ROI reconstruction is often needed, and so it may be preferred that the energy-adjusted correction is added to the original projections to form a new set of corrected projections.

At 420, method 400 may include reconstructing an image from the energy-adjusted projections. Any suitable image reconstruction algorithm may be used, including but not limited to filtered back projection as well as iterative image reconstruction algorithms. The image reconstructed from the energy-adjusted projections includes contrast-enhancements.

At 425, method 400 may include outputting the final reconstructed image. The final reconstructed image may be output, for example, to mass storage 218 or in non-transitory memory of computer 216 for subsequent blending with a multi-material corrected image as described herein above with regard to FIG. 3. Method 400 may then end.

FIG. 6 is a high-level flow chart illustrating an example method 600 for reconstructing an image from projection data modified by a multi-material correction according to an embodiment of the invention. Method 600 may comprise a subroutine of method 300. In particular, method 600 may comprise the step 340 of method 300. Thus, the projection data acquired at 305, the forward projection of the re-mapped image volume at 325, the selected energy received at 330, and so on may be available for use during the execution of method 600. Method 600 may be carried out using the systems and components depicted in FIGS. 1 and 2, however the method may be applied to other systems and components without departing from the scope of the present disclosure.

Method 600 may begin at 605. At 605, method 600 may include determining detection coefficients for each pixel of the detector array 108, for example as described hereinabove with regard to FIG. 4. In one example, step 605 and step 405 may comprise the same step while methods 400 and 600 run in parallel. In another example, the detection coefficients for each pixel of the detector array 108 may be determined at 405 and stored in memory 218 for retrieval. In such an example, determining the detection coefficients may comprise retrieving the stored detection coefficients.

At 610, method 600 may include computing a material linearization function for each pixel. The detection coefficients may be utilized in computing a material linearization function (for example, a mapping function) or a beam hardening projection error for each pixel using projections synthesized through system modeling. The mapping function for each pixel is designed to linearize material projections for the respective pixel. In general, the detected signals may be re-mapped so that the signals are all linearly proportional to each of the material's length with proper slope. The slope is a fixed value for each individual material that does not change from view to view. The slope assigned to each material may in principle be any value. However, in practice, the slope should be very close to the attenuation coefficient at the effective energy (i.e., keV) of the beam. This keeps the correction small enough that the original noise is maintained and, therefore, is more forgivable to errors in the material segmentation and characterization. As mentioned above, the mapping function for multi-material correction is based on individual pixels. This individual pixel-based approach removes general physics beam hardening and variation in detector spectral response or absorption. In one example, the mapping function may be generated based on two basis materials, for example water and iodine. Other basis material pairs may be selected from other materials such as calcium, metal, bone, and so on. The use of two basis materials enables a complex body composition to be simplified into two components. This reduces the need for forward projections for other materials (i.e., those not selected as the basis materials), while also reducing the complexity of the mapping function.

At 615, method 600 may include generating multi-material corrected projections for each pixel based on the material-based projection obtained at step 325 of method 300 and the initial total projection (e.g., the projection data acquired at 305) representing attenuation through both of the two basis materials (e.g., iodine and water). In particular, the multi-material corrected projections may be based on a summation of the initial total projection and the material linearization function computed herein above at 610. In some examples, the initial total projection and the linearization function may be subtracted from each other. The linearization function is based on the values for the material-based projection and the initial total projection. In some embodiments, the initial total projection may be a spectrally corrected total raw projection.

At 620, method 600 may include reconstructing an image from the multi-material corrected projections. At 625, method 600 may include outputting the final reconstructed image. Method 600 may then end.

A technical effect of the disclosure may include the generation of a contrast-enhanced image reconstructed from projection data acquired at a single energy. Another technical effect of the disclosure may include the simulation of a low energy acquisition based on projection data acquired at a higher energy. Yet another technical effect of the disclosure may include the display to a user of a contrast-enhanced image without beam hardening artifacts. Another technical effect of the disclosure may include the blending of two images, wherein one image includes contrast-enhanced regions and the other image is substantially free of beam hardening artifacts.

In one embodiment, a method comprises modifying projection data corresponding to a material based on an absorption behavior of the material at a selected energy, wherein the projection data is acquired at an energy higher than the selected energy. In one example, the selected energy is selected by a user based on the material.

In one example, the method further comprises: acquiring the projection data at the energy; reconstructing the projection data into a reconstructed image; performing material characterization of the reconstructed image to reduce a number of materials in the reconstructed image to at least two basis materials; generating a re-mapped image for at least one basis material of the at least two basis materials; performing forward projection on at least the re-mapped image for the at least one basis material to produce a material-based projection; and wherein modifying the projection data corresponding to the material is based on the material-based projection.

In another example, the method further comprises generating an image based on the modified projection data and blending the image with a second image reconstructed from a second set of modified projection data to generate a final image. The method further comprises displaying the final image to a user. In yet another example, the second set of modified projection data comprises multi-material corrected projections based on the material-based projection.

In one example, blending the image with the second image comprises selecting a Hounsfield unit for an image volume based on the image, the second image, and a soft threshold. In another example, the method further comprises segmenting the reconstructed image, and wherein blending the image with the second image is based on the segmented reconstructed image.

In one example, the two basis materials comprise iodine and water, and the at least one basis material and the material comprise iodine.

In another example, modifying the projection data comprises: determining detection coefficients for each of a plurality of pixels of a detector; computing mapping functions at the selected energy for each of the plurality of pixels based on the detection coefficients; and generating energy-adjusted projections based on the mapping functions.

In another embodiment, a method comprises: reconstructing projection data acquired at a given energy into a reconstructed image; performing material characterization of the reconstructed image to reduce a number of materials in the reconstructed image to two basis materials; generating a re-mapped image for at least one basis material of the two basis materials; performing forward projection on at least the re-mapped image for the at least one basis material to produce a material-based projection; modifying the projection data corresponding to the at least one basis material based on an absorption behavior of the at least one basis material at a selected energy, wherein the selected energy is lower than the given energy; generating multi-material corrected projections based on the material-based projection wherein the multi-material corrected projections comprise linearized projections; and blending the modified projection data and the multi-material corrected projections based on the material-based projection to generate a final image.

In one example, the at least one basis material comprises iodine. In another example, the selected energy is selected by a user.

In some examples, the method further comprises segmenting the reconstructed image. Blending the modified projection data and the multi-material corrected projections is based on the segmented reconstructed image.

In one example, modifying the projection data comprises: determining detection coefficients for each of a plurality of pixels of a detector; computing mapping functions at the selected energy for each of the plurality of pixels based on the detection coefficients; and generating energy-adjusted projections based on the mapping functions.

In another example, performing material characterization of the reconstructed image comprises performing inverse basis material decomposition on the reconstructed image to convert materials other than the two basis materials to the two basis materials.

In yet another embodiment, a system comprises: an x-ray source that emits a beam of x-rays toward an object to be imaged, the beam of x-rays comprising x-rays at an acquisition energy; a detector that receives the x-rays attenuated by the object; a data acquisition system (DAS) operably connected to the detector; and a computer operably connected to the DAS and programmed with instructions in non-transitory memory that when executed cause the computer to: modify projection data corresponding to a material based on an absorption behavior of the material at a selected energy, wherein the selected energy is lower than the acquisition energy.

In one example, the system further comprises a display, and the computer is further programmed with instructions in the non-transitory memory that when executed cause the computer to display an image generated based on the modified projection data. In another example, the image is further generated based on a second modified projection dataset, the second modified projection dataset comprising multi-material corrected projections.

In another example, the system further comprises an operator console operably connected to the computer, and the selected energy is received from the operator console.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring projection data via a detector that receives x-rays generated by an x-ray source at an acquisition energy;
   modifying the projection data corresponding to a material based on an absorption behavior of the material at a selected energy, wherein the acquisition energy is higher than the selected energy;
   reconstructing an image based on the modified projection data; and
   generating a final image from the reconstructed image.

2. The method of claim 1, wherein the selected energy is selected by a user based on the material.

3. The method of claim 1, further comprising:
   reconstructing the projection data into a reconstructed image;
   performing material characterization of the reconstructed image to reduce a number of materials in the reconstructed image to at least two basis materials;
   generating a re-mapped image for at least one basis material of the at least two basis materials;
   performing forward projection on at least the re-mapped image for the at least one basis material to produce a material-based projection; and
   wherein modifying the projection data corresponding to the material is based on the material-based projection.

4. The method of claim 3, further comprising blending the image with a second image reconstructed from a second set of modified projection data to generate a final image.

5. The method of claim 4, further comprising displaying the final image to a user.

6. The method of claim 4, wherein the second set of modified projection data comprises multi-material corrected projections based on the material-based projection.

7. The method of claim 4, wherein blending the image with the second image comprises selecting a Hounsfield unit for an image volume based on the image, the second image, and a soft threshold.

8. The method of claim 4, further comprising segmenting the reconstructed image, and wherein blending the image with the second image is based on the segmented reconstructed image.

9. The method of claim 3, wherein the two basis materials comprise iodine and water, and the at least one basis material and the material comprise iodine.

10. The method of claim 1, wherein modifying the projection data comprises:
    determining detection coefficients for each of a plurality of pixels of a detector;
    computing mapping functions at the selected energy for each of the plurality of pixels based on the detection coefficients; and
    generating energy-adjusted projections based on the mapping functions.

11. The method of claim 1, further comprising blending the image with a second image reconstructed from a second set of modified projection data to generate the final image.

12. The method of claim 11, further comprising reconstructing an image from the projection data and segmenting the reconstructed image, wherein blending the image with the second image is based on the segmented reconstructed image.

13. A method, comprising:
    reconstructing projection data acquired via a detector that receives x-rays generated by an x-ray source at a given energy into a reconstructed image;

performing material characterization of the reconstructed image to reduce a number of materials in the reconstructed image to two basis materials;

generating a re-mapped image for at least one basis material of the two basis materials;

performing forward projection on at least the re-mapped image for the at least one basis material to produce a material-based projection;

modifying the projection data corresponding to the at least one basis material based on an absorption behavior of the at least one basis material at a selected energy, wherein the selected energy is lower than the given energy;

generating multi-material corrected projections based on the material-based projection wherein the multi-material corrected projections comprise linearized projections; and blending the modified projection data and the multi-material corrected projections based on the material-based projection to generate a final image.

14. The method of claim 13, wherein the at least one basis material comprises iodine.

15. The method of claim 13, wherein the selected energy is selected by a user.

16. The method of claim 13, further comprising segmenting the reconstructed image, and wherein blending the modified projection data and the multi-material corrected projections is based on the segmented reconstructed image.

17. The method of claim 13, wherein modifying the projection data comprises:

determining detection coefficients for each of a plurality of pixels of a detector;

computing mapping functions at the selected energy for each of the plurality of pixels based on the detection coefficients; and generating energy-adjusted projections based on the mapping functions.

18. The method of claim 13, wherein performing material characterization of the reconstructed image comprises performing inverse basis material decomposition on the reconstructed image to convert materials other than the two basis materials to the two basis materials.

19. A system, comprising:

an x-ray source that emits a beam of x-rays toward an object to be imaged, the beam of x-rays comprising x-rays at an acquisition energy;

a detector that receives the x-rays attenuated by the object;

a data acquisition system (DAS) operably connected to the detector; and a computer operably connected to the DAS and programmed with instructions in non-transitory memory that when executed cause the computer to:

acquire projection data at the acquisition energy;

modify the projection data corresponding to a material based on an absorption behavior of the material at a selected energy, wherein the selected energy is lower than the acquisition energy; and generate an image based on the modified projection data.

20. The system of claim 19, further comprising a display, and wherein the computer is further programmed with instructions in the non-transitory memory that when executed cause the computer to display the image generated based on the modified projection data.

21. The system of claim 20, wherein the image is further generated based on a second modified projection dataset, the second modified projection dataset comprising multi-material corrected projections.

22. The system of claim 19, further comprising an operator console operably connected to the computer, wherein the selected energy is received from the operator console.

* * * * *